(12) United States Patent
Pritzke et al.

(10) Patent No.: US 9,033,005 B2
(45) Date of Patent: May 19, 2015

(54) DEVICE FOR INTRODUCING A DEFINED AMOUNT OF A SECOND POWDER INTO A PROCESS CONTAINER

(71) Applicants: Glatt Systemtechnik GmbH, Dresden (DE); Harro Hoefliger Verpackungsmaschinen GmbH, Allmersbach im Tal (DE)

(72) Inventors: Heinz Pritzke, Kesselsdorf (DE); Reiner Wurst, Auenwald (DE); Wolfgang Knorr, Dresden (CZ)

(73) Assignees: Glatt Systemtechnik GmbH, Dresden (DE); Harro Hoefliger Verpackungsmaschinen GmbH, Allmersbach Im Tal (DE)

( * ) Notice: Subject to any disclaimer, the term of this patent is extended or adjusted under 35 U.S.C. 154(b) by 0 days.

(21) Appl. No.: 14/242,017

(22) Filed: Apr. 1, 2014

(65) Prior Publication Data
US 2014/0311627 A1    Oct. 23, 2014

(30) Foreign Application Priority Data
Apr. 19, 2013    (DE) .......................... 10 2013 104 003

(51) Int. Cl.
*B65B 1/06*        (2006.01)
*G01F 11/28*       (2006.01)
(Continued)

(52) U.S. Cl.
CPC ................ *B65B 1/06* (2013.01); *G01F 11/282* (2013.01); *B65B 1/38* (2013.01); *A61M 5/31596* (2013.01); *G01F 11/003* (2013.01)

(58) Field of Classification Search
CPC ............. F16K 27/0218; B01F 15/0237; B01F 14/002; G01J 8/002; B65B 39/00; G01F 11/14; G01F 11/16; G01F 11/18; G01F 11/24
USPC ......... 141/100, 114, 318, 319, 320, 322, 346, 141/363, 380, 383, 81, 107, 113, 137, 231, 141/284, 307, 339, 340; 222/380, 387
See application file for complete search history.

(56) References Cited

U.S. PATENT DOCUMENTS 395,138 A * 12/1888 Heineman ...................... 141/319
487,886 A * 12/1892 Hausman ........................ 73/429
(Continued)

FOREIGN PATENT DOCUMENTS

DE    2143403    8/1972
DE    2062516    2/1979
(Continued)

*Primary Examiner* — Jason K Niesz
*Assistant Examiner* — Andrew Schmid
(74) *Attorney, Agent, or Firm* — Jordan and Hamburg LLP

(57) ABSTRACT

An apparatus to introduce a defined amount of a second powder into a process container in which a first powder or a powder mixture is present, includes a coupling flange having a cover flap located on the process container. The second powder is introduced into a tubular cartridge mounted displaceably in a transport unit, the latter including a joining flange having a cover flap. The joining flange is joinable to the coupling flange so that the respective cover flaps can be opened, and the cartridge can be pushed through openings thereby provided into the plane of the inner wall of the process container. The second powder is emptied from the cartridge into the process container by a delivery piston. The cartridge may include a piston rod having multiple pistons. Other embodiments include a double piston, a rotatable cartridge core or a rotary closure.

13 Claims, 7 Drawing Sheets

(51) Int. Cl.
*B65B 1/38* (2006.01)
*A61M 5/315* (2006.01)
*G01F 11/00* (2006.01)

(56) References Cited

U.S. PATENT DOCUMENTS

| | | | | |
|---|---|---|---|---|
| 576,241 A * | 2/1897 | Van Ame | | 222/308 |
| 677,667 A * | 7/1901 | Kirschen | | 222/387 |
| 762,800 A * | 6/1904 | Bowden | | 222/305 |
| 795,676 A * | 7/1905 | Ammen | | 222/308 |
| 933,528 A * | 9/1909 | Bruce | | 222/308 |
| 1,047,722 A * | 12/1912 | Vergano | | 222/42 |
| 1,229,396 A * | 6/1917 | Andres | | 222/284 |
| 1,233,656 A * | 7/1917 | Fetner | | 222/365 |
| 1,233,791 A * | 7/1917 | Kaiser | | 222/308 |
| 1,638,456 A * | 8/1927 | Pike | | 222/340 |
| 2,035,182 A * | 3/1936 | Morgan | | 73/232 |
| 2,161,190 A * | 6/1939 | Paull | | 222/252 |
| 2,393,382 A * | 1/1946 | Kerr | | 141/107 |
| 2,571,083 A * | 10/1951 | Wilt | | 222/184 |
| 3,064,858 A * | 11/1962 | Ziegler | | 222/49 |
| 3,301,443 A * | 1/1967 | Clancy et al. | | 222/380 |
| 3,823,853 A * | 7/1974 | Alden | | 222/365 |
| 4,023,715 A * | 5/1977 | Biondo | | 222/307 |
| 5,154,212 A * | 10/1992 | Weber | | 141/353 |
| 5,348,060 A * | 9/1994 | Futagawa et al. | | 141/100 |
| 5,411,175 A * | 5/1995 | Armstrong et al. | | 222/83.5 |
| 5,490,546 A * | 2/1996 | Lhoest | | 141/346 |
| 5,769,824 A * | 6/1998 | Hjertman et al. | | 604/143 |
| 5,881,357 A * | 3/1999 | Takemoto et al. | | 419/38 |
| 5,924,417 A * | 7/1999 | Braithwaite | | 128/203.15 |
| 6,283,176 B1 * | 9/2001 | Wurst et al. | | 141/144 |
| 6,374,875 B1 * | 4/2002 | Schroeder et al. | | 141/322 |
| 6,828,577 B2 * | 12/2004 | Zens | | 250/515.1 |
| 7,588,062 B1 * | 9/2009 | Green | | 141/362 |
| 7,913,720 B2 * | 3/2011 | Tribble et al. | | 141/27 |
| 2004/0031819 A1 * | 2/2004 | Smiley | | 222/449 |
| 2006/0086761 A1 * | 4/2006 | Yang | | 222/344 |
| 2006/0261095 A1 * | 11/2006 | Rebordosa et al. | | 222/234 |
| 2007/0113924 A1 * | 5/2007 | Phillips | | 141/351 |
| 2008/0098776 A1 * | 5/2008 | Pritzke et al. | | 70/158 |
| 2009/0001101 A1 * | 1/2009 | Zahradka et al. | | 222/228 |
| 2009/0090431 A1 * | 4/2009 | Yacko et al. | | 141/26 |
| 2010/0065579 A1 * | 3/2010 | DiPerna | | 222/1 |
| 2010/0193548 A1 * | 8/2010 | Poreda et al. | | 222/365 |
| 2011/0204088 A1 * | 8/2011 | Luchinger | | 222/77 |
| 2011/0212519 A1 | 9/2011 | Wilson et al. | | |
| 2012/0055270 A1 * | 3/2012 | Pritzke | | 73/864.51 |
| 2012/0160873 A1 * | 6/2012 | Hsu et al. | | 222/321.1 |
| 2012/0175384 A1 * | 7/2012 | Greter et al. | | 222/137 |
| 2012/0292348 A1 * | 11/2012 | Thulin | | 222/361 |
| 2014/0261876 A1 * | 9/2014 | Mansour et al. | | 141/27 |
| 2014/0311627 A1 * | 10/2014 | Pritzke et al. | | 141/284 |

FOREIGN PATENT DOCUMENTS

| | | |
|---|---|---|
| DE | 2917189 | 4/1981 |
| DE | 3104062 | 1/1982 |
| DE | 4342962 | 2/1995 |
| DE | 202005015569 | 1/2006 |
| DE | 10 2006 061 992 | 6/2008 |
| DE | 202009018738 | 1/2013 |
| EP | 0447023 | 7/1994 |
| EP | 2 184 590 | 5/2010 |
| EP | 2 508 219 | 10/2012 |
| WO | WO 2007039378 A1 * | 4/2007 ............... B29B 7/76 |

* cited by examiner

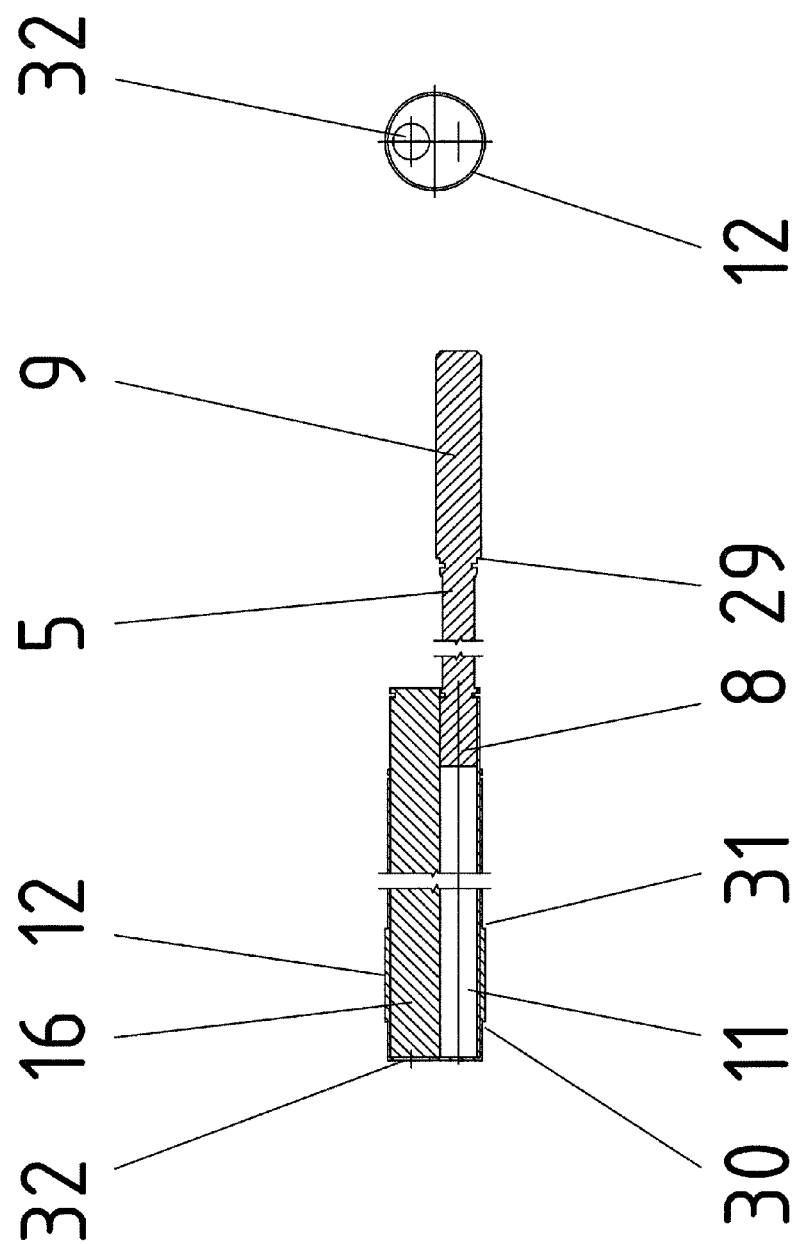

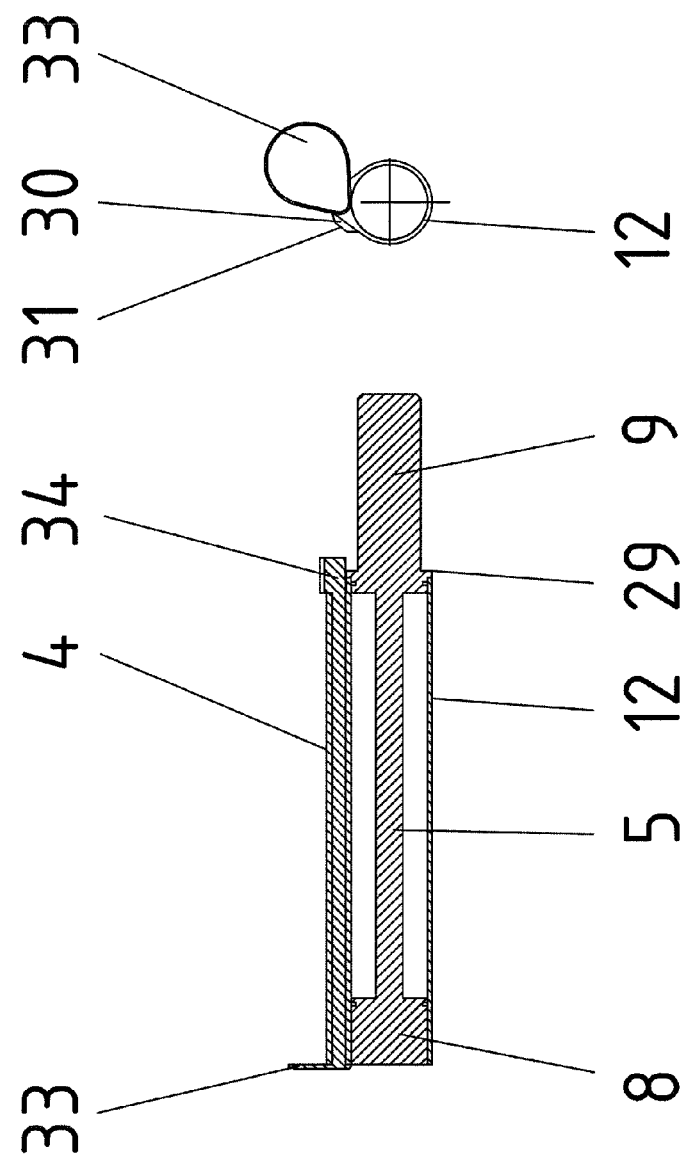

DEVICE FOR INTRODUCING A DEFINED AMOUNT OF A SECOND POWDER INTO A PROCESS CONTAINER

BACKGROUND OF THE INVENTION

The invention relates to a device for introducing a defined amount of a second powder into a process container in which a first powder or a powder mixture is present. The device is provided in particular for charging small and minute amounts of powdered substances into larger process containers, in particular for admixing low amounts of powdered active pharmaceutical substances to main components already present in a process container, such as lactose or corn starch. The invention is particularly suited for containment applications of active substances and/or sterile applications.

According to the prior art, the addition of certain components into mixing containers is known to be carried out by simple pouring via an opening in the lid. For this purpose, a pocket-size metering device for pourable goods as described in the unexamined patent application DE 21 43 403 can be used. The hand-held metering device is used only for the metered dispensing of artificial sweetener due to the low precision of the device, although it was intended for powdered pharmaceuticals.

Another device for mixing a blend of pulverized constituents is described in DE 3 104 062 A1, for example. A second powder is introduced into the fluidized bed of a first powder. This is carried out under pressure by impinging the second pulverized constituent onto a deflection plate disposed within the fluidized bed for uniform distribution of the second constituent therein.

A metering device acting according to the principle of gravity is described in DE 2 917 189 B2, for example. For volumetrically metering free-flowing powders in batches using a storage container and a double piston metering unit comprising a piston rod having an upper piston and a lower piston, the lower piston of which can move away from the upper piston, the lower piston moves away from the upper piston during an upward movement of the piston rod and approaches the upper piston during the downward movement of the piston rod, whereby the volume of the constriction present between the upper and lower pistons increases to a predetermined extent during the upward movement and decreases to the predetermined metering volume during the downward movement before passing the dosing chamber.

Another option for adding is to carry out the charging via an opening in the lid by way of long mixing lances extending into the mixed bed.

DE 20 62 513 B2 describes a device for volumetrically metering free-flowing powder in batches, comprising a vertically disposed piston rod that is provided with a constriction as the feed control device. Metering devices of this type have the disadvantage of low precision in terms of the metered amounts of powder.

So as to meet a general requirement that is placed on pipe couplings, according to which each half of the coupling comprises a respective valve which can be opened when the coupling halves are properly joined to each other and which must be moved so as to be fully closed before the respective halves of the coupling can be separated from each other, EP 0 447 023 B1 describes a dry break coupling for lines having two valve flaps that can be actuated separately from each other.

DE 20 2009 018 738 U1 discloses an easy-to-detach coupling system for axially coupling two parallel flanges, in which the end faces of the two flanges are axially pressed against each other for coupling purposes, and in which two coupling halves comprise rotatably mounted closing flaps, which are seated against each other in a planar manner after the coupling has been established and can be opened together.

DE 4 342 962 C1 describes a device for coupling two containers which each have a connecting pipe neck, in which each of the pipe necks comprises a closing flap close to the end facing away from the container supporting the neck, the closing flap being essentially pivotable by 90° about a diameter of the pipe neck, the outside diameter thereof essentially corresponding to the inside diameter of the pipe neck.

An added substance metering device for a polyurethane plant for introducing a defined amount of a second substance into a process container in which a first substance or a substance mixture is present is known from DE 20 2005 015 569 U1, wherein the substance can be introduced into a cartridge 10 that is inserted into a holder and equipped with a quick-action coupling and can be emptied by way of a delivery piston 26.

SUMMARY OF THE INVENTION

When pharmaceuticals are produced, the components to be mixed have very large differences in terms of the quantities. Minute amounts (0.01 to 1%) of powdered active pharmaceutical substances must be admixed to the main components in exactly defined dosages.

When such low amounts are to be admixed, there is a risk that losses that occur during addition already result in a very high mixing ratio deviation, on a percentage basis. These losses may occur directly in the process container or at the metering devices. During addition from above into the process container by way of an open metering device, powdered substances may deposit on the side walls and other surfaces present in the process container. Direct losses on metering devices may be caused by large surfaces or long stroke lengths, such as with the above-described metering lances, for example. For example, if 20 g of active substances are to be admixed to a process container holding 60 liters and containing approximately 20 kg of main components, a loss of just 2 g would result in inadmissible undercharging of 10% of active substances. It is therefore advantageous if charging is performed with the shortest route, and if possible directly into the mixed bed, which is to say below the fill level in the process container.

It is the object of the invention to provide a device which allows very small amounts of powdered substances to be charged into larger process containers without losses or contamination. The charging is to take place with simple means and high metering accuracy. The invention is particularly suited for containment applications of active substances and/or sterile applications.

The invention is described hereafter in general as well as in greater detail in conjunction with the described embodiments of the invention, including the drawings.

According to the invention, a defined amount of a second powder is introduced into a process container, in which a first powder or a powder mixture is already present, through a coupling flange, which is located on the process container and comprises a cover flap, and the second powder can be introduced into a tubular cartridge, which can be mounted displaceably in a transport unit. The transport unit comprises a joining flange having a cover flap, wherein the joining flange can be joined to the coupling flange so that the two cover flaps can be opened. The cartridge can be displaced within the transport unit through openings provided by opening the cover flaps. The front discharge opening of the cartridge, or the end of an included delivery piston, should preferably extend into the plane of the inner wall of the process container. The second powder to be metered can then be emptied from the cartridge into the process container by way of the delivery piston.

In an advantageous embodiment, the coupling flange can be composed of a connecting piece and a flap valve. Both parts can be fixedly or detachably joined to each other.

In a further advantageous embodiment, the joining flange can be composed of a cartridge holder and a flap valve. Both parts can likewise be fixedly or detachably joined to each other.

In one embodiment of the invention, the cartridge comprises a cartridge sleeve, in the inner powder chamber of which the delivery piston is disposed on the delivery side so as to be displaceable by way of an actuatable piston rod. On the container side, the cartridge can be closed by a closing piston that is displaceably disposed on the same piston rod.

In a further embodiment of the invention, the cartridge comprises a cartridge sleeve, in the inner powder chamber of which a double piston is displaceably disposed. The delivery piston can be displaced by way of a first piston rod, while the cartridge can be closed on the container side by way of a closing piston that is disposed so as to be displaceable by way of a second piston rod. Both pistons can be actuated separately from each other.

A special embodiment of the invention relates to a cartridge that comprises a cartridge sleeve, in which a cartridge core that can be rotated axially by at least 100° is disposed. A powder chamber, in which a delivery piston is disposed so as to be displaceable by way of a piston rod, extends over the entire length of the cartridge core. The cartridge sleeve has a discharge opening on the container side. So as to empty the cartridge, the powder chamber can be rotated so far over the discharge opening that the two openings are sufficiently aligned for the powder to be emptied into the process container.

A preferred embodiment is implemented in a device in which the cartridge comprises a cartridge sleeve into which a rotary closure can be laterally integrated, by way of which a discharge opening of the cartridge can be closed by way of an actuating lever. The cartridge sleeve is preferably oval for this purpose. This embodiment has the advantage that no separate closing piston is required.

In all the embodiments, the amount of product that can be metered or emptied from the cartridge is determined by the stroke and the diameter of the powder chamber.

So as to safely fill the cartridge with a defined amount of powder material, the entire transport unit can be removed and transported to a separate location. A flexible protective casing should therefore be attached to the joining flange, so that the protective casing completely encloses the inserted cartridge. The purpose of this is that the system also remains closed when the cartridge is removed from the transport unit prior to filling, and that no special seal is required between the cartridge and the cartridge holder.

So as to introduce the powder to be metered, the joining flange of the transport unit and the coupling flange are joined to each other, wherein the respective cover flaps thereof should seal tightly with each other and be pivotable together. The outsides of the cover flaps thus remain free of powder. This ensures operator safety in terms of containment.

Instead of a closing piston, the cartridge can be closed at the discharge opening thereof by a penetrable membrane. The membrane is preferably made of a material that is the same as one of the components of the powders to be mixed in the process container. If the membrane were made of other substances, such as paper or plastic, one would have to ensure that no foreign substances can be charged into the process container, which could result in undesirable additions or contamination.

An automated process is advantageous in particular for containment applications of active substances or sterile applications. The device can be designed for this purpose so that the delivery piston is coupled by way of a detachable connection to a drive that causes automatic metering or emptying. The drive can be an electric or servo-pneumatic drive.

By using small cartridges having exactly defined amounts of ingredients, precise micrometering is made possible. Possible charging from the cartridge directly below the fill level of the mixed bed ensures addition without losses, as the powder material cannot deposit on the walls. The design of the adding device likewise ensures that no deposition or adherence can take place within the device. The device is directed to containment applications of active substances and/or sterile applications.

The invention will be described in greater detail hereafter based on several exemplary embodiments.

BRIEF DESCRIPTION OF THE DRAWINGS

FIGS. 4a, 4b show a cartridge comprising a rotatable cartridge core;

FIGS. 5a, 5b show a cartridge comprising a rotary closure;

DETAILED DESCRIPTION OF THE INVENTION

For mixing components for the production of pharmaceuticals in a containment system, for example, approximately 20 g of powdered active substances is to be admixed to a process container 1 which holds 60 liters, in which approximately 20 kg of powdered substances of one or more main components, such as lactose or corn starch, are present.

Figure 1:
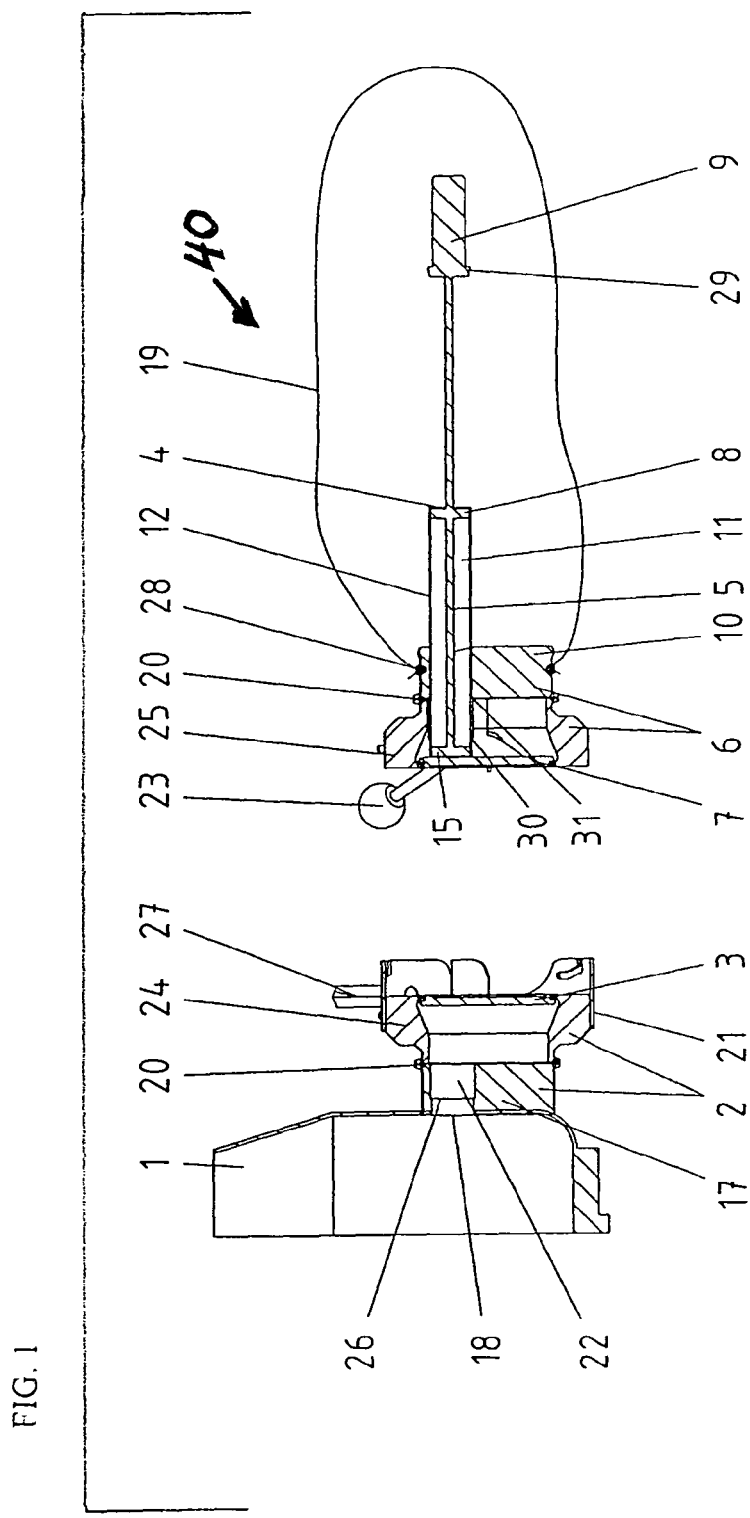
FIG. 1 is a sectional view of a device according to the invention, comprising a connecting unit and a decoupled transport unit, into which a cartridge is pushed up to the cover flap, which is still closed.

A first exemplary embodiment is illustrated in FIG. 1. The device according to FIG. 1 shows a coupling flange 2 on the left and a transport unit 40 comprising an inserted cartridge 4 on the right. The transport unit 40 also serves as a transport means from the filling complex to the metering station for the process container 1.

Cartridges having very small diameters are used for minute amounts to be metered. The stroke and the diameter of the delivery piston 8 and the inside diameter of the powder chamber 11 determine the amount of product that can be metered or emptied from the cartridge. In the example described here, an approximately 190 mm long cartridge having an inside diameter of the cartridge sleeve 12 of 34 mm is used.

The transport unit 40 comprises a joining flange 6, which is designed as two pieces for the sake of production and cleaning. The flange comprises a cartridge holder 10, and a flap valve 25 of the kind set out in EP 0 447 023 B1. Both parts are detachably joined to each other by way of a clamp 20. The cartridge holder 10 has a bore for accommodating the cartridge 4. This bore can be used to allow the precisely filled cartridge 4 to be pushed through an opening provided by opening the cover flap 7 of the flap valve 25. In FIG. 1, the cartridge 4 is only pushed up to the cover flap 7, wherein the cover flap 7 and the protective casing 19 tightly seal the joining flange 6 for secure transport. The cover flap 7 of the flap valve 25 can be operated by way of a lever mechanism 23.

The coupling flange 2 remains on the process container 1 as a permanent connecting unit. The coupling flange 2 is preferably designed as two pieces so as to allow easy production and better cleaning of the two parts. In the present exemplary embodiment, the flange comprises a connecting piece 17 and a flap valve 24 according to the principle set out in EP 0 447 023 B1. Both parts are detachably joined to each other by way of a clamp 20. The connecting piece 17 is attached to the process container 1 so that the inner side forms part of the process container. For example, the piece can be welded on or screwed on. The connecting piece 17 has a bore 22, up to which the cartridge 4 can be pushed through the opened cover flap 3 of the flap valve 24 to the inner wall of the process container 1. The cover flap 3 is shown still closed in FIG. 1. In the present example, the connecting piece 17 comprises a projection 26, which serves as a stop for the cartridge sleeve 12. The diameter of the discharge opening 18 corresponds to the outside diameter of the cartridge 4.

The cover flaps 3, 7 of the two flap valves 24, 25 can be jointly operated by way of the lever mechanism 23 when they are installed. After the cover flaps 3, 7 are opened, a passage for the cartridge 4 is created above and beneath the cover flaps 3, 7. The two bores in the connecting piece 17 and in the cartridge holder 10 for accommodating the cartridge 4 must be accordingly aligned. This is ensured by customary fixations for positioning, such as centering pins.

In the device according to FIG. 1, two parallel flanges are axially coupled according to the principle described in DE 20 2009 018 738 U1, wherein the end faces of the two flanges are axially pressed against each other for coupling purposes and fixed by way of a coupling sleeve 21 that can be operated by an actuating lever 27.

In FIG. 1, the cartridge 4 comprises a cartridge sleeve 12, in the inner powder chamber 11 of which the delivery piston 8 is disposed on the delivery side so as to be displaceable by way of an actuatable piston rod 5. On the container side, the cartridge 4 can be closed by a closing piston that is disposed on the same piston rod 5. So as to protect the transport unit both during transport and during the actual metering operation, a groove is incorporated into the cartridge holder 10, a flexible protective casing 19, which is so large that it extends around the handle 9 of the extended piston rod 5 of the cartridge 4, being securable in this groove by way of a retaining ring 28. The protective casing 19 is made of a transparent plastic film.

The operating principle is as follows:

After the cartridge 4 has been filled separately with the required amount of product as described in FIG. 7, the entire transport unit is connected in the manner described above to the corresponding flap valve 24 of the coupling flange 2 and is secured with the coupling sleeve 21. Thereafter the two cover flaps 3 and 7 are opened and the cartridge 4 is pushed into the coupling flange 2 so far that the first stop 30 of the cartridge sleeve 12 strikes against the projection 26. The cartridge sleeve 12 and the front side of the closing piston 15 close the bore 18 in the process container 1. Thereafter the process can start and the metering of the main powder component can be carried out.

So as to meter the powder that is present in the cartridge 4, the piston rod is pressed, together with the closing piston 15 and the delivery piston 8, in the direction of the process container, by way of the handle 9, until the handle stop 29 strikes against the cartridge sleeve 12, and the front end of the delivery piston 8 ends in the plane of the inner wall of the process container 1.

The piston rod 5 and the closing piston 15 located therein protrude into the process container. Since the charging site is located below the fill level in the process container 1, the powder to be metered is entrained by the powder mixture of the main components that is already present in the process container 1 during the mixing process that takes place in the process container, and is homogeneously distributed.

After the material has been added and the mixing process has ended, and after the process container 1 has been completely emptied, the piston rod 5 is again retracted into the cartridge 4. The cartridge 4 is then retracted until the second stop 31 strikes against the cartridge holder 10 and the two cover flaps 3 and 7 can be closed.

After the two flanges have been decoupled, the transport unit is removed for refilling of the cartridge 4.

Figure 2:
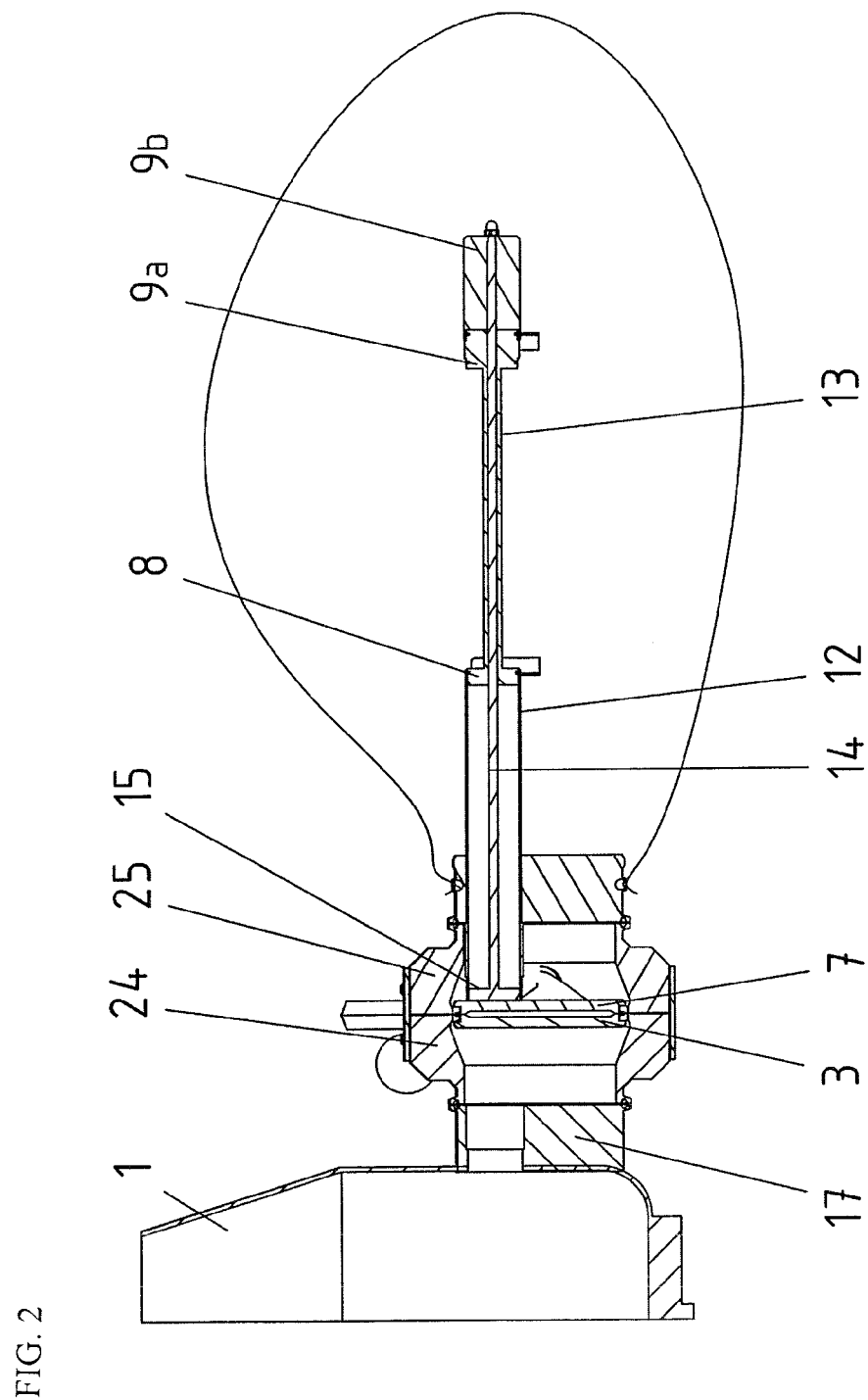
FIG. 2 shows a device with a double piston solution.

Another exemplary embodiment is shown in FIG. 2 and in FIGS. 3a to 3d. FIG. 2 shows a cartridge 4 with a double piston solution.

The cartridge 4 is filled and introduced into the transport unit through the two flap valves 25 and 24 and the connecting piece 17 up to the inner wall of the process container, analogously to the exemplary embodiment of FIG. 1. The cartridge 4 that is used again comprises a closing piston 15 and a delivery piston 8 inside the cartridge sleeve 12. However, the difference here is that the two pistons can each be actuated with a separate piston rod. In the illustrated example, the inner closing piston 15 is attached to the inner piston rod 14 and can be operated by way of the right handle part 9b. The delivery piston 8 is attached to the outer piston rod 13 and can be operated by way of the left handle part 9a.

FIGS. 3a to 3d show the operating principle of a double piston solution described in FIG. 2.

Figure 3A:
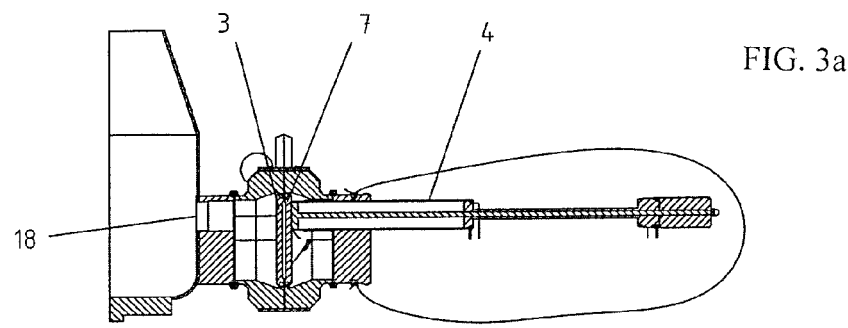
FIGS. 3a to 3d show a device with a double piston solution in four different positions.

In FIG. 3a, the filled cartridge 4, which is closed with the closing piston 15, is inserted up to the cover flap 7.

Figure 3B:
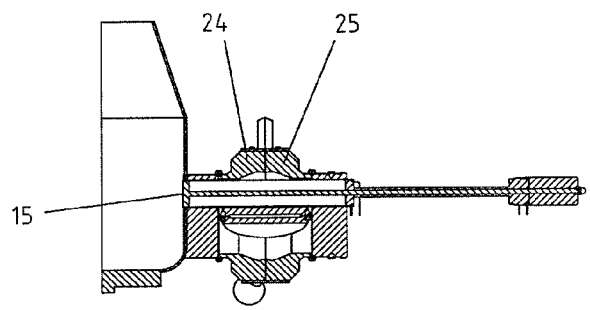

In FIG. 3b, the cartridge 4 penetrates the flap valves 25 and 24, with the cover flaps 3 and 7 being open. The closing piston 15 still closes the discharge opening 18. The two pistons are still located in the same position as in FIG. 3a.

Figure 3C:
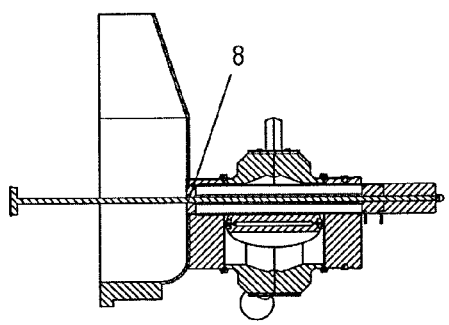

Thereafter the cartridge 4 can be emptied by the joint insertion of the two pistons until the front end of the delivery piston 8 ends in the plane of the inner wall of the process container 1. In FIG. 3c, the cartridge 4 has already been emptied in this position. It is also possible to push in only a defined portion of the closing piston 15 and then empty the cartridge 4 with the delivery piston 8. Retraction of the closing piston 15, as is shown in FIG. 3d, is then no longer necessary.

Figure 3D:
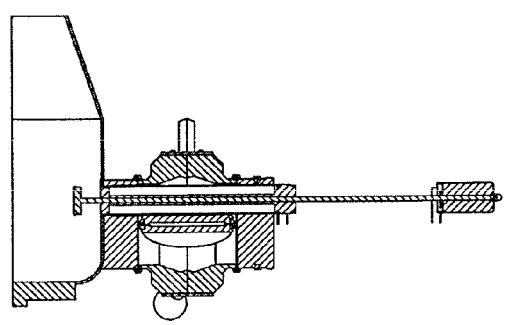
Figure 6A:
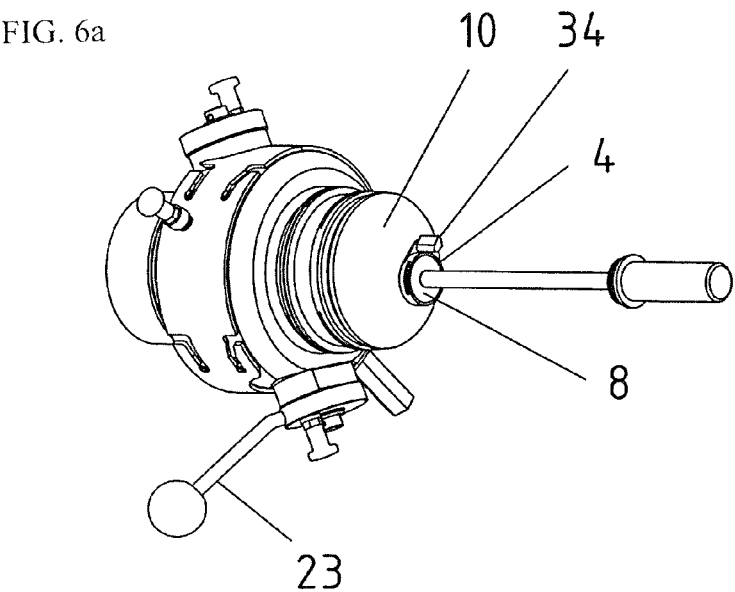
FIGS. 6a, 6b show perspective illustrations of a device comprising a rotary closure.
Figure 6B:
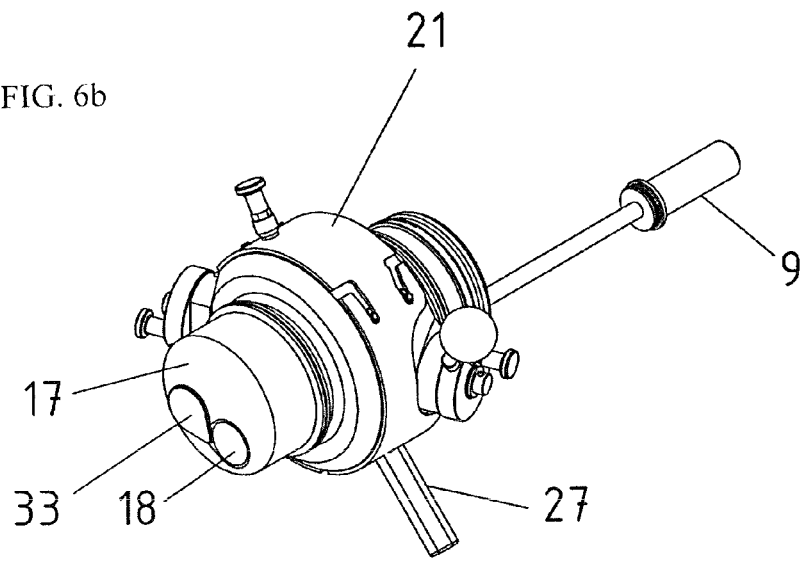

It can be seen in FIG. 3d that the closing piston 14 can be retracted separately from the delivery piston 8 after emptying. The closing piston 15 must only be retracted until it reaches a short distance in front of the delivery piston 8, so far that no amounts of product remain in the pistons. The process is ended in this position, the process container 1 is emptied, and the cartridge 4 is retracted as described in FIG. 1.

FIGS. 4a, 4b show a special embodiment of a cartridge 4. A cartridge core 16, which can be axially rotated by at least 100°, is located inside a cartridge sleeve 12. The powder chamber 11 extends over the entire length of the cartridge core 16. The delivery piston 8 is disposed so as to be displaceable in the powder chamber 11 by way of the piston rod 5. FIG. 4 shows the cartridge 4 in the closed state. So as to empty the cartridge 4, the cartridge core 16 is rotated until the powder chamber 11 is aligned with the opening 32 located on the end face of the cartridge sleeve 12 and releases the powder material contained therein into the process container. The delivery piston 8 is pushed up to the handle stop 29 against the cartridge core 16, so that the front end of the delivery piston 8 ends in the plane of the inner wall of the process container 1.

The cartridge 4 described here likewise has a length of 190 mm and the inside diameter of the cartridge sleeve 12 is 34 mm. However, since the powder chamber 11 has a diameter of only 12 mm, more exact metering of considerably smaller metering amounts can be achieved.

As in the preceding examples, the cartridge 4 can be inserted into the transport unit and the coupling flange and can be used.

A further embodiment of the device according to the invention is apparent from FIGS. 5a, 5b and FIGS. 6a and 6b. Here a variant is shown in which a round delivery piston 8 is disposed so as to be displaceable by way of a piston rod 5 and a handle 9 attached thereto in the interior of the cartridge sleeve 12 in the above-described manner. A handle stop 29 is located on the handle 9 and is positioned so that the front end of the pushed-in delivery piston 8 ends in the plane of the inner wall of the process container 1 when it is empty, as can be seen in FIG. 5.

However, the tubular cartridge 4 shown here has an oval cartridge sleeve 12, in the lateral molded extension of which a rotary closure 33 is integrated. The rotary closure comprises a shaft which is integrated into the lateral molded extension, at the front end of which a cover flap is provided. An actuating lever 34 is located at the rear end of the shaft and can be used to pivot the cover flap over the discharge opening 18 and completely seal the same.

So as to implement this embodiment, it is necessary for both the connecting piece 17 and the cartridge holder 10 to have an inner oval shape, which corresponds to the contour of the cartridge sleeve 12 and allows the cartridge 4 to be pushed in.

This embodiment has the advantage that a separate closing piston is no longer required. After metering, no closing piston thus remains in the process container, and the discharge opening 18 can be closed.

In this embodiment as well, the cartridge 4 can only be removed after the process container 1 has been emptied.

Figure 7A:
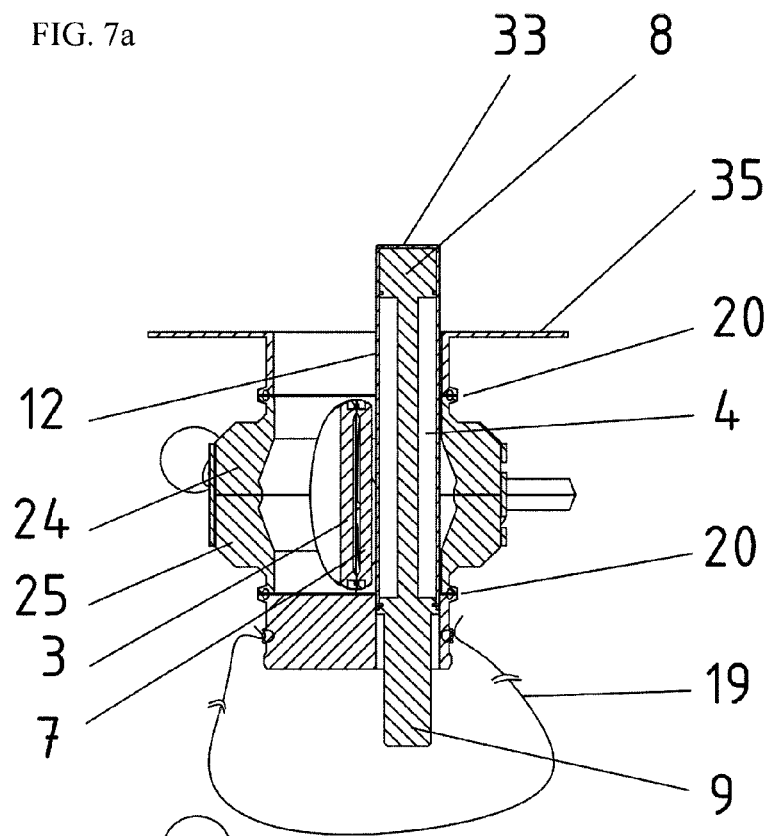
FIGS. 7a, 7b are illustrations of the cartridge filling process.
Figure 7B:
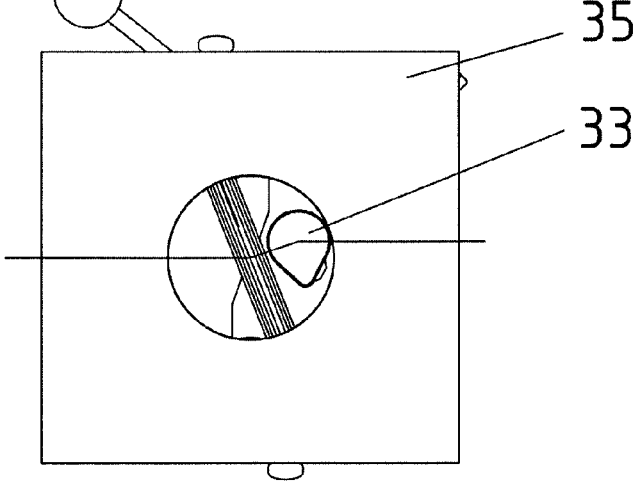

FIGS. 7a, 7b show a transport unit that is connected to a filling complex, in which a cartridge having a rotary closure 33 according to FIG. 5 is used. The filling complex comprises a glovebox, a weighing system having a cartridge holder, and a micro-metering system for filling (all not shown).

A rigid connecting flange 35, to which a flap valve 24 designed in the above-described manner was attached by way of a clamp 20, is present on the filling complex. After the transport unit has been coupled, the two cover flaps 3 and 7 are opened by way of the respective lever mechanisms thereof. Since the connecting flange 35 on the filling system does not comprise a projection 26, the emptied cartridge 4 can then be pushed into the filling complex through the two cover flaps 3 and 7 of the flap valves 25 and 24 and removed. In FIGS. 7a, 7b, the emptied cartridge 4 is in the process of being pushed out of the transport unit into the filling complex, and the rotary closure 33 is closed. There, the cartridge can be cleaned and refilled under containment conditions. The filled cartridge 4 is returned into the transport unit in the reverse order.

The invention claimed is:

1. An apparatus for introducing a defined amount of a second powder into a process container in which a first powder or a powder mixture is present, the apparatus being configured to be coupled to the process container, the apparatus comprising;
   a coupling flange comprising a first cover flap, the coupling flange being configured to be removably attached to the process container;
   a tubular cartridge without an opening along the outer circumference to define a volume for containing the second powder; and
   a transport unit for displaceably mounting the cartridge;
   wherein the transport unit comprises a joining flange having a second cover flap;
   wherein the joining flange is removably joined to the coupling flange to achieve a configuration in which the first and second cover flaps can be opened;
   wherein the cartridge has a distal end surface configured to be in a plane of an inner wall of the process container;
   wherein the transport unit further comprises a delivery piston movable within the tubular cartridge; and
   wherein the transport unit and tubular cartridge are configured to empty the second powder from the cartridge into the process container when the tubular cartridge is positioned by the transport unit to occupy respective openings in said coupling flange and joining flange, said respective openings being uncovered by said first and second cover flaps, respectively.

2. The apparatus according to claim 1, wherein the coupling flange comprises a connecting piece and a flap valve.

3. The apparatus according to claim 1, wherein the joining flange comprises a cartridge holder and a flap valve.

4. The apparatus according to claim 1, wherein the cartridge comprises a cartridge sleeve having an inner powder chamber in which the delivery piston is disposed so as to be displaceable by way of an actuatable piston rod, and the cartridge is closable at a distal end of the cartridge adapted to abut the container by a closing piston that is disposed so as to be displaceable by way of the actuatable piston rod.

5. The apparatus according to claim 1, wherein the cartridge comprises a cartridge sleeve having an inner powder chamber in which the delivery piston is disposed so as to be displaceable by way of an actuatable piston rod, and the cartridge is closable at a distal end of the cartridge adapted to abut the container by a closing piston that is disposed so as to be displaceable by way of a second actuatable piston rod.

6. The apparatus according to claim 1, wherein the cartridge comprises a cartridge sleeve in which a cartridge core rotatable about an axis by at least 100° is disposed;
   a powder chamber extending over length of the cartridge core and in which the delivery piston is disposed so as to be displaceable by way of a piston rod is provided;
   the cartridge sleeve has a discharge opening at a distal end of the cartridge sleeve adapted to abut the container; and
   so as to empty the cartridge, the cartridge core is rotatable until the powder chamber aligns with the discharge opening.

7. The apparatus according to claim 1, wherein the cartridge comprises a cartridge sleeve onto a side of which a rotary closure is integrated, a discharge opening of the cartridge sleeve being closable by the rotary closure by way of an actuating lever.

8. The apparatus according to claim 1, further comprising a flexible protective casing attached to the joining flange so that a proximal portion of the cartridge projecting from the joining flange when a distal end of the cartridge is abutting the flap of the joining flange is completely enclosed by the flexible protective casing.

9. The apparatus according to claim 1, wherein the cover flaps seal tightly with each other and are pivotable together when the joining flange and the coupling flange are joined.

10. The apparatus according to claim 1, wherein the delivery piston is coupled to a drive, which causes automatic metering or emptying, by way of a releasable linkage.

11. The apparatus according to claim 4, wherein the actuatable piston rod, delivery piston, and closing piston are located within the tubular cartridge.

12. The apparatus according to claim 5, wherein the actuatable piston rod, delivery piston, and closing piston are located within the tubular cartridge.

13. The apparatus according to claim 1, further comprising a lever that actuates movement of the first cover flap and the second cover flap.

* * * * *